United States Patent [19]

Paul

[11] Patent Number: 5,164,384

[45] Date of Patent: Nov. 17, 1992

[54] ANABOLIC MINERAL FORMULA

[75] Inventor: Steven M. Paul, San Clemente, Calif.

[73] Assignee: Metagenics, Inc., San Clemente, Calif.

[21] Appl. No.: 717,550

[22] Filed: Jun. 19, 1991

[51] Int. Cl.⁵ .................. A61K 31/555; A23L 1/30
[52] U.S. Cl. ............................ 514/188; 514/356; 426/72; 426/74; 426/648; 426/804
[58] Field of Search ............... 514/188, 356; 426/72, 426/74, 648, 804

[56] References Cited

U.S. PATENT DOCUMENTS

| | | | |
|---|---|---|---|
| 4,315,927 | 2/1982 | Evans | 514/188 |
| 4,897,220 | 1/1990 | Donzis | 514/356 |
| 5,023,358 | 7/1991 | Lazaro | 556/42 |

OTHER PUBLICATIONS

Pharmacol Toxicol, (1990 Sep.) 67 (3) 192-8, Mongold et al., "Toxicological Aspects of Vanadyl Sulfate . . . Effects of Vanadium Leads Bad Panereatic B-Cell Morphology" Abstract.

*Primary Examiner*—Marianne M. Cintins
*Assistant Examiner*—Rebecca Cook
*Attorney, Agent, or Firm*—Stetina and Brunda

[57] ABSTRACT

The present invention is an ergogenic, anabolic mineral formula for use as a nutritional supplement, weight loss formula and cholesterol lowering agent. The formula comprises 500 mcg. of vanadyl sulfate, 100 mcg. of chromium picolinate, 100 mcg. of chromium nicotinate glycinate, and 25 mg. of niacin. The vanadyl sulfate and chromium components are used primarily to mimic and enhance the effects of insulin. The niacin component is included to cause blood vessels to dilate and to reduce cholesterol levels and thus improve the efficiency of chromium and carbohydrate utilization.

9 Claims, No Drawings

ANABOLIC MINERAL FORMULA

FIELD OF THE INVENTION

The present invention relates generally to dietary supplements, and more particularly to an ergogenic anabolic mineral formula comprising vanadyl sulfate, chromium and niacin, for use as a nutritional supplement, weight loss formula, and cholesterol lowering agent.

BACKGROUND OF THE INVENTION

As is well known in the medical community, insulin is one of the most powerful anabolic hormones in the body and is the primary driver of amino acids and glucose into muscle cells. In muscle tissue, insulin initiates the transport of glucose, mineral ions and amino acids, and also regulates the synthesis and degradation of macromolecules. Additionally, insulin decreases muscle catabolism during exercise which allows greater gains from intense exercise. It has been found that increased insulin activity affects tissues, and in particular muscle tissue, in a manner such that increased protein synthesis and muscle growth can occur.

Although insulin is primarily known for its ability to promote tissue uptake of blood sugar, i.e. glucose, it exerts a number of other important physiologioal effects. These effects include increased synthesis and retention of protein in skeletal muscle and other tissues; stimulation of activated immune cells; enhanced brain uptake of tyrosine and tryptophan (precursors for important brain neurotransmitters); reduced output of free-fatty acids from adipose stores; accelerated potassium uptake by cells; and increased metabolic rate. Additionally, insulin mediates the thermogenic effects of carbohydrates which typically cause increases in metabolic rate following absorption of dietary carbohydrates. Such mediation occurs through the activation by the insulin of fat burning in "brown fat". Insulin is also required for proper thyroid function, and stimulates activity of the "sodium pump", an enzyme that regulates ion movements and accounts for a significant fraction of the metabolic energy burned everyday. Studies have indicated a tendency for mature adults to lose sensitivity to insulin. A sedentary lifestyle, overweightness, and an over-refined diet (i.e. low fiber, low chromium, high in sugars) all contribute to decreased insulin sensitivity. Studies have also found that individuals with impaired insulin sensitivity are at risk for high blood pressure, hypertension, heart disease and diabetes.

Numerous scientific studies have found that vanadyl sulfate and chromium, when ingested, have properties that closely mimic as well as enhance many of the physiologioal effects of insulin. In this respect, it has been found that these elements serve to both increase the effectiveness and enhance the anabolic effects of insulin. Supplementation of these elements into a normal diet has been shown to increase lean body mass without increasing body fat, stabilize blood sugar, i.e. glucose levels, increase, the responsiveness of cells to insulin and lower blood fat levels. By their ability to potentiate the effects of insulin, both vanadyl sulfate and chromium have been found to enhance the entry of glucose (for energy) and amino acids (for protein synthesis) into muscle cells and inhibit the action of enzymes that catabolize the amino acids and proteins. It has further been found that these particular elements include cholesterol lowering, energy producing and anabolic promoting properties which provide an optimal environment for anabolic development, weight/fat loss and energy output.

Though a large number of dietary supplements are currently known and marketed, no such supplements include a novel mixture of vanadyl sulfate and chromium so as to enhance and mimic the positive effects that insulin has on the body's metabolism. The present invention overcomes these and other deficiencies associated with the prior art.

SUMMARY OF THE INVENTION

In accordance with a preferred embodiment of the present invention, there is provided an ergogenic anabolic mineral formula for use as a nutritional supplement, weight loss formula and cholesterol lowering agent. The formula preferably comprises 25 mg. of niacin, 100 mcg. of chromium picolinate, 100 mcg. of chromium nicotinate glycinate, and 500 mcg. of vanadyl sulfate.

The vanadyl sulfate and chromium compounds utilized in the aforementioned formula have been shown to share several key anabolic effects of insulin and to enhance the effects of insulin by stimulating key metabolic pathways. The vitamin niacin is also included in the formula in order to improve the efficiency of chromium and carbohydrate utilization. Importantly, the three aforementioned anabolic mineral ingredients work together in the present formula to enhance the effectiveness of insulin in tissues, thereby increasing the potential for an anabolic state leading to muscle growth. The formula is preferably taken with meals or whenever carbohydrates are ingested to maximize the anabolic effects leading to muscle growth. Additionally, the formula is preferably provided in tablet form though it may also be provided in powder or liquid form.

DETAILED DESCRIPTION OF THE PREFERRED EMBODIMENT

The following discussion is included for purposes of discussing a preferred embodiment of the present invention and is not intended to limit the scope of the present invention in any manner.

The present invention comprises an ergogenic, anabolic mineral formula for use as a dietary supplement. The formula is intended for use as a nutritional supplement, weight loss formula and cholesterol lowering agent. The manner in which the formula provides these three specific effects will be discussed in greater detail below. The formula comprises 1 mg. to 3,000 mg. of niacin, 1 mcg. to 1,000 mcg. of chromium picolinate, 1 mcg. to 1,000 mcg. of chromium nicotinate glycinate and 1 mcg. to 1,000 mcg. of vanadyl sulfate. The preferred formula comprises 25 mg. of niacin, 100 mcg. of chromium picolinate, 100 mcg. of chromium nicotinate glycinate and 500 mcg. of vanadyl sulfate.

The present formula is preferably provided in tablet form though it will be appreciated that such may also be provided in powder or liquid form. For the desired results, the proper dosages are from one (1) to thirty (30) tablets daily.

The vanadyl sulfate, chromium and niacin composition of the present formula serves to mimic as well as enhance a number of beneficial effects of insulin, thereby increasing the effectiveness of and enhancing its anabolic effects. Such effects include the inhibition of the enzyme phosphotransferase which serves to preserve the phosphorylated state of sugar for insulin uptake and action; the stimulation of glucose transport; the activation of glycogen synthase; and an increase in tissue responsiveness to insulin. As such, the present formula possesses insulin-like effects and mimics both the glucose transport-dependent and the intracellular actions of insulin in adipocytes and in skeletal muscle. Thus, by potentiating the effects of insulin, the present formula enhances the entry of glucose and amino acids into muscle cells thereby promoting muscle development. The specific ingredients of the present formula and the manner in which the ingredients facilitate the insulin mimicing and enhancing effects of the present formula will now be discussed.

VANADYL SULFATE COMPONENT

The compound vanadyl sulfate, once ingested, typically forms vanadate which is a salt of vanadic acid. It has been found that vanadate ions will mimic all or most of the actions of insulin in intact cell systems via a post-receptor mechanism. In various tissues, certain metabolic effects of insulin require phosphorylatian reactions. Phosphorylation generally means a metabolic process of introducing a phosphate group into an organic molecule. For example, when insulin binds the fat cells, it causes phosphorylation of the amino acids threonine, tyrosine and serine in the insulin receptors of the fat cells and thus stimulates glucose transport, glycogen synthesis and glucose oxidation. It has been found that vanadate, like insulin, also causes phosphorylation of the insulin receptors of fat cells and thus stimulates glucose transport, activates glycogen synthase, and increases glycogen syntheses in the fat cells. Indeed, experimental studies have concluded that vanadata and insulin cause qualitatively similar changes in muscle glucose metabolism. These studies have also indicated that the ability of vanadate to mimic insulin action may be attributed to either the anion's ability to participate in reduction-oxidation processes, or to regulate (inhibit) phosphotransferase activity.

It has been found that vanadate stimulates carbohydrate uptake in the liver. In contrast, insulin does not stimulate glucose transport in this tissue, although insulin binding and stimulation of diverse biochemical processes have been previously demonstrated. Additionally, it has also been found that vanadate does not increase serum insulin levels, which therefore suggests that insulin target tissues themselves are not the site of vanadate action.

As previously indicated, vanadate is operable to activate glycogen synthase. Glycogen synthase is an enzyme which causes the conversion of glucose into glycogen. Glycogen itself is a polysaccharide which is the chief carbohydrate storage material in humans. It has been found that maximum glycogen synthase activation produced by vanadate is indistinguishable from that of insulin. Evidence that strongly suggests a common mechanism of action for insulin and vanadate includes the following findings: with maximum insulin, additional quantities of vanadate are without effect; with submaximal insulin, additional quantities of vanadate increase both the glycogen synthase activation state and 2-deoxyglucose transport to the level obtained with maximum insulin; insulin and vanadate counteract the activating effect of adrenalin on glycogen phosphorylase in a similar manner; adrenalin partially reverses vanadate and insulin activated glycogen synthase in a similar manner; and vanadate and insulin activate glycogen synthase within similar time frames. Thus, the presence of in-vivo vanadate from the ingestion of vanadyl sulfate can lead to stable, long lasting, normoglycemic and anabolic states and restore tissue responsiveness to insulin without apparent signs of toxicity.

CHROMIUM COMPONENT

Chromium levels in biological matter have been studied extensively. It has been found that chromium produces significant increases in enzyme activity and serves an important function in carbohydrate metabolism, stimulation of fatty acid and cholesterol synthesis from acetate in liver, and improved sugar metabolism through the activation of insulin. Additionally, it has been found that chromium renders the body's tissues more sensitive to insulin.

Like vanadyl sulfate, chromium possesses properties which both mimic and enhance the effects of insulin. When enhancing the effects of insulin, chromium indirectly assists amino acid uptake by muscle, stimulates protein synthesis and retards the rate of protein breakdown. Additionally, by normalizing blood sugar, biologically active chromium may break the cycle of alternating hyper- and hypoglycemia with its consequence of overeating and weight gain. There have been many anecdotal reports that chromium can curb sugar cravings. Additionally, by promoting insulin-stimulated brain uptake of tryptophan, it has also been found that chromium may aid brain synthesis of serotonin, a neurotransmitter that helps control appetite and especially sugar cravings. Additionally, since insulin stimulates protein synthesis and retards protein breakdown in skeletal muscle and other tissues, the chromium potentiation of this effect could be especially valuable to dieter's by burning fat and in athletes for the development of muscle.

Previous clinical studies with supplemental chromium have shown modest improvements in glucose tolerance. A prime reason for the realization of only modest improvements is attributed to the relatively poor absorption of nutritional (trivalent) chromium. In this respect, trivalent chromium has a strongly positive charge that impedes its movement a ross cell membranes. Due to the presence of competing ions such as copper, iron, manganese and zinc in the human body, adequate absorption of chromium occurs only when the metal is associated with a specific organic molecule. This particular organic molecule is picolinic acid which is a natural chelating agent. Picolinic acid is a metabolite of tryptophan produced in the liver and kidneys. Additionally, picolinic acid may also be synthesized from certain yeast, i.e. brewer's yeast. Because of its unique structure, picolinic acid has a strong affinity for transition metals such as zinc, manganese, and chromium. In this respect, it binds tightly to these metals, thereby neutralizing their positive charges and expediating their movement across cell membranes. Chromium picolinate is a biologically active form of chromium. In chromium picolinate, the picolinic acid serves as an effective metal chelator that improves the utilization and uptake of the chromium and plays an important physiological roll in trace mineral absorption. Because several investigations have implicated chromium as a regulatory component in lipid and carbohydrate metabolism, it is generally assumed that the chromium ion is the active factor while the picolinic acid serves as the chelator to improve bioavailability. Animal studies with chromium picolinate have shown it to be five to ten times better absorbed and retained than other forms of chromium tested and have also found it to be remarkably safe. In various studies, chromium picolinate was also found to have an anabolic effect. Additional studies have shown that there are several mechanisms by which chromium picolinate may help maintain a high metabolic rate and thereby aid in weight loss. These are, an increased rate at which a special type of fat, i.e. "brown fat" is burned; better thyroid function; and stimulation of the body's "sodium pump" which consumes a large fraction of the calories consumed each day.

The chromium nicotinate glycinate ingredient of the present formula is primarily utilized to aid in the decrease of cholesterol levels.

NIACIN COMPONENT

As previously indicated, niacin is incorporated into the present formula primarily for purposes of improving the efficiency of chromium and carbohydrate utilization. Niacin is often recommended as the first drug of choice when dietary intervention fails to adequately reduce elevated LDL cholesterol levels. Niacin is also effective in decreasing triglycerides in total cholesterol. Additionally, the vasodilating properties of niacin have been used to enhance blood flow in a variety of vascular disturbances, including conditions where vasospasms are considered to be part of the problem. Thus, as used in the present formula, niacin is important for its ability to cause blood vessels to dilate and its ability to reduce cholesterol levels.

Additional modifications and improvements of the present invention may also be apparent to those skilled in the art. Thus, the particular combination of parts described and illustrated herein is intended to represent only one embodiment of the invention, and is not intended to serve as limitations of alternative devices within the spirit and scope of the invention.

What is claimed is:

1. An ergogenic, anabolic mineral composition for use as a nutritional supplement, weight loss formula and cholesterol lowering agent, comprising:
   from 1 mg. to 3,000 mg. of niacin;
   from 1 mcg. to 1,000 mcg. of chromium picolinate;
   from 1 mcg. to 1,000 mcg. of chromium nicotinate glycinate; and
   from 1 mcg. to 1,000 mcg. of vanadyl sulfate.

2. The composition of claim 1 comprising 25 mg. of niacin.

3. The composition of claim 1 comprising 100 mcg. of chromium picolinate.

4. The composition of claim 1 comprising 100 mcg. of chromium nicotinate glycinate.

5. The composition of claim 1 comprising 500 mcg. of vanadyl sulfate.

6. An ergogenic anabolic minerals composition for use as a nutritional supplement, weight loss formula and cholesterol lowering agent, comprising:
   25 mg. of niacin;
   100 mcg. of chromium picolinate;
   100 mcg. of chromium nicotinate glycinate; and
   500 mcg. of vanadyl sulfate.

7. The composition of claim 6 wherein said formula is in the form of a tablet.

8. The formula of claim 6 wherein said composition is in the form of a powder.

9. The formula of claim 6 wherein said composition is in the form of a liquid.

* * * * *